United States Patent
Hwang et al.

(10) Patent No.: US 10,336,680 B2
(45) Date of Patent: Jul. 2, 2019

(54) PROCESS FOR PREPARING BIS(2-HYDROXYETHYL) TEREPHTHALATE

(71) Applicant: FAR EASTERN NEW CENTURY CORPORATION, Taipei (TW)

(72) Inventors: Der-Ren Hwang, Taipei (TW); Cheng-Ting Wang, Taipei (TW); Hsiao-Chan Wang, Taipei (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 1 day.

(21) Appl. No.: 15/729,996

(22) Filed: Oct. 11, 2017

(65) Prior Publication Data

US 2019/0002388 A1    Jan. 3, 2019

(30) Foreign Application Priority Data

Jul. 3, 2017  (TW) .............. 106122190 A

(51) Int. Cl.
| | | |
|---|---|---|
| *C07C 67/26* | (2006.01) | |
| *C07C 67/54* | (2006.01) | |
| *C07C 69/82* | (2006.01) | |
| *C07C 67/035* | (2006.01) | |

(52) U.S. Cl.
CPC ............ *C07C 67/26* (2013.01); *C07C 67/035* (2013.01); *C07C 67/54* (2013.01); *C07C 69/82* (2013.01)

(58) Field of Classification Search
CPC ....... C07C 67/26; C07C 67/035; C07C 67/54; C07C 69/82
See application file for complete search history.

(56) References Cited

U.S. PATENT DOCUMENTS

| | | |
|---|---|---|
| 3,052,711 A | 9/1962 | Glogau et al. |
| 3,706,785 A * | 12/1972 | Larkin ................... C07C 69/80 560/93 |
| 6,310,233 B1 | 10/2001 | Maurer et al. |
| 7,332,548 B2 | 2/2008 | White et al. |

* cited by examiner

*Primary Examiner* — Pancham Bakshi
*Assistant Examiner* — Mark R Luderer
(74) *Attorney, Agent, or Firm* — Osha Liang LLP

(57) ABSTRACT

A process for preparing bis(2-hydroxyethyl) terephthalate, comprising a step of: subjecting ethylene oxide and terephthalic acid in a molar ratio of from 2:1 to 3:1 to a reaction at an elevated temperature in the presence of a solvent mixture containing water and a $C_6$-$C_8$ hydrocarbon in a weight ratio of from 1:1 to 3:1.

9 Claims, No Drawings

PROCESS FOR PREPARING BIS(2-HYDROXYETHYL) TEREPHTHALATE

CROSS-REFERENCE TO RELATED APPLICATION

This application claims priority of Taiwanese Application No. 106122190, filed on Jul. 3, 2017.

FIELD

The disclosure relates to a process for preparing bis(2-hydroxyethyl) terephthalate, and more particularly to a process for preparing bis(2-hydroxyethyl) terephthalate at an elevated temperature in the presence of a solvent mixture.

BACKGROUND

In a process for preparing polyethylene terephthalate (referred to as PET hereinafter), bis(2-hydroxyethyl) terephthalate (referred to as BHET hereinafter) having Formula (1) below is prepared, followed by polycondensation of BHET to prepare PET.

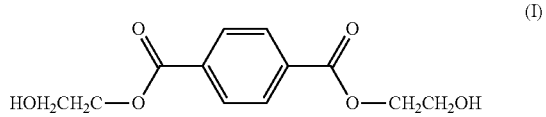

(I)

In the industry, BHET may be prepared by subjecting ethylene oxide and terephthalic acid to a reaction so as to avoid problems encountered in a transesterification process in which methanol is produced as an undesirable byproduct and problems encountered in an esterification process which requires a pressurized atmosphere and addition of a significant amount of glycol, and which results in a product containing undesirable oligomer.

U.S. Pat. No. 3,052,711 discloses a process for the preparation of di(β-hydroxyethyl) terephthalate (i.e., BHET) by the reaction of ethylene oxide with terephthalic acid. A reaction mass is formed by continuously feeding ethylene oxide and a slurry prepared from terephthalic acid, water, and a water-soluble base into one end of a heated reaction zone. Possibility of production of glycol by the reaction of water with ethylene oxide may be reduced, and the problem of hydrolysis of BHET may be avoided. However, a waste solvent which has to be further processed is in an amount of about 1 kg per kg of BHET.

U.S. Pat. No. 7,332,548 discloses a process to produce a partially esterified carboxylic acid product, which comprises contacting at least one di carboxylic acid with at least one alkylene oxide in a reactor zone in the presence of at least one solvent and at least one basic catalyst. The solvent includes at least one selected from toluene and xylene. However, as shown in Table 5, conversion of esterified terephthalic acid is below 54.4%.

U.S. Pat. No. 6,310,233 discloses a process for reacting dicarboxylic acid with alkylene oxide to produce hydroxyalkyl ester monomers and perhaps minor amounts of oligomers, A mixture of water with dimethyl ether is used as a solvent in the process. However, a primary product produced in the process is mono(2-hydroxyethyl) terephthalate of Formula (2), rather than BHET.

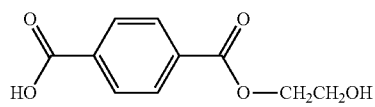

(2)

SUMMARY

An object of the disclosure is to provide a process for preparing bis(2-hydroxyethyl) terephthalate to overcome the aforesaid shortcomings.

According to an aspect of the disclosure, there is provided a process for preparing bis(2-hydroxyethyl) terephthalate, comprising a step of:

subjecting ethylene oxide and terephthalic acid in a molar ratio of from 2:1 to 3:1 to a reaction at an elevated temperature in the presence of a solvent mixture containing water and a $C_6$-$C_8$ hydrocarbon in a weight ratio of from 1:1 to 3:1.

DETAILED DESCRIPTION

A process for preparing bis(2-hydroxyethyl) terephthalate, comprising steps of:

(a) subjecting ethylene oxide and terephthalic acid in a molar ratio of from 2:1 to 3:1 to a reaction at an elevated temperature in the presence of a solvent mixture containing water and a $C_6$-$C_8$ hydrocarbon in a weight ratio of from 1:1 to 3:1; and (b) removing the solvent mixture.

In certain embodiments, the molar ratio of ethylene oxide to terephthalic acid is from 2.7:1 to 3:1.

In certain embodiments, the solvent mixture is in an amount from 3 to 10 mole based on 1 mole of terephthalic acid. In the following illustrative examples, the solvent mixture is in an amount from 3.3 to 4.5 mole based on 1 mole of terephthalic acid.

In certain embodiments, the $C_6$-$C_8$ hydrocarbon is selected from the group consisting of hexane, heptane, octane, cyclohexane, benzene, toluene, xylene, and combinations thereof. In certain embodiments, the $C_6$-$C_8$ hydrocarbon is selected from the group consisting of cyclohexane, toluene, and a combination thereof.

In certain embodiments, the reaction is performed in the presence of a base. In certain embodiments, the base is selected from the group consisting of sodium carbonate, potassium carbonate, sodium hydroxide, potassium hydroxide, amine, an organic ammonium salt, an inorganic ammonium salt, and combinations thereof. In the following illustrative examples, the base is sodium carbonate.

In certain embodiments, step (a) is implemented by combining terephthalic acid with the solvent mixture to form a combination and adding ethylene oxide to the combination slowly at the elevated temperature.

In certain embodiments, the elevated temperature for performing the reaction is in a range from 100° C. to 150° C. In the following illustrative examples, the elevated temperature is about 120° C.

In certain embodiments, the reaction of ethylene oxide with terephthalic acid is performed at a pressure from 5 kgf/cm² to 15 kgf/cm². In the following illustrative examples, the reaction of ethylene oxide with terephthalic acid is performed at a pressure from 5 kgf/cm² to 7 kgf/cm².

In certain embodiments, in step (d), the solvent mixture is removed via distillation at a reduced pressure.

Examples of the disclosure will be described hereinafter. It is to be understood that these examples are exemplary and explanatory and should not be construed as a limitation to the disclosure.

Example 1

Terephthalic acid (345 g, 2.077 mol), sodium carbonate (3.89 g), water (103.5 g), and toluene (103.5 g) were added into a 1 L stainless reactor (total amount of water and toluene: 207 g, 6.873 mol), followed by heating under stirring to a temperature of 120° C. and slowly adding ethylene oxide at a flow rate of 1 ml/min at a temperature of 120° C. under a pressure below 7.0 kgf/cm2 until 274.4 g (6.230 mol) of ethylene oxide was added. A reaction was carried out for 15 minutes, followed by lowering of the temperature to 110° C., removal of water and toluene via distillation under a reduced pressure, and cooling to room temperature to obtain a coarse product containing BHET.

Examples 2-4

The procedure of Example 1 was repeated except that the amounts of ethylene oxide used in Examples 2-4 were 247.0 g (5.607 mol), 228.7 g (5.192 mol), and 183.0 g (4.154 mol), respectively.

Example 5

The procedure of Example 1 was repeated except that 247.0 g (5.607 mol) of ethylene oxide, 155.25 g of water, and 51.75 g of toluene were used. The total amount of water and toluene was 207 g (9.187 mol).

Example 6

The procedure of Example 1 was repeated except that 247.0 g (5.607 mol) of ethylene oxide, 155.25 g of water, and 51.75 g of cyclohexane were used. The total amount of water and cyclohexane was 207 g (6.980 mol). Water and cyclohexane were removed after the reaction.

Comparative Example 1

The procedure of Example 1 was repeated except that 247.0 g (5.607 mol) of ethylene oxide and 207 g (11.5 mol) of water were used, and toluene was not added. Water was removed after the reaction.

Comparative Example 2

The procedure of Example 1 was repeated except that 247.0 g (5.607 mol) of ethylene oxide, 51.75 g of water, and 155.25 g of toluene were used. The total amount of water and toluene was 207 g (4.560 mol).

The amounts of ethylene oxide, terephthalic acid, water, and toluene or cyclohexane used in Examples 1-6 and Comparative Examples 1 and 2 are summarized in Table 1 below.

TABLE 1

| | Reactants | | | Solvents | | | |
|---|---|---|---|---|---|---|---|
| | Ethylene oxide (mol) | Terephthalic acid (mol) | Molar ratio[1] | Water (g) | Hydrocarbon (g) | Weight ratio[2] | Total amount (mol) |
| Ex. 1 | 6.230 | 2.077 | 3 | 103.5 | Toluene 103.5 | 1 | 6.873 |
| Ex. 2 | 5.607 | 2.077 | 2.7 | 103.5 | Toluene 103.5 | 1 | 6.873 |
| Ex. 3 | 5.192 | 2.077 | 2.5 | 103.5 | Toluene 103.5 | 1 | 6.873 |
| Ex. 4 | 4.154 | 2.077 | 2 | 103.5 | Toluene 103.5 | 1 | 6.873 |
| Ex. 5 | 5.607 | 2.077 | 2.7 | 155.25 | Toluene 51.75 | 3 | 9.187 |
| Ex. 6 | 5.607 | 2.077 | 2.7 | 103.5 | Cyclohexane 103.5 | 1 | 6.980 |
| Comp. Ex. 1 | 5.607 | 2.077 | 2.7 | 207 | — | — | 11.5 |
| Comp. Ex. 2 | 5.607 | 2.077 | 2.7 | 51.75 | Toluene 155.25 | 0.33 | 4.560 |

Note:
[1]Molar ratio of ethylene oxide to terephthalic acid
[2]Weight ratio of water to hydrocarbon Analysis of Conversion of Terephthalic Acid:

Conversion of terephthalic acid in each of Examples 1-6 and Comparative Examples 1 and 2 was analyzed via 1H NMR (300 MHz, solvent: dimethyl sulfoxide). The results are shown in Table 2 below.

Analysis of MHET (Byproduct):

A molar ratio of MHET to BHET in the coarse product obtained in each of Examples 1-6 and Comparative Examples 1 and 2 was analyzed via HPLC (high performance liquid chromatography, solvent: a mixture of methanol with water in a weight ratio of 7:3; sample amount: 10 µl; wavelength: 254 nm; flow rate: 200 µl/min; three mobile phases in sequence: (1) a first mobile phase: a mixture of water with methanol in a volume ratio of 9:1 for 5 minutes, (2) a second mobile phase: a mixture of water with methanol in a linear gradient from a volume ratio of 9:1 to a volume ratio of 2:8 over 35 minutes, and (3) a third mobile phase: a mixture of water with methanol in a volume ratio of 2:8 for 5 minutes). The results are shown in Table 2.

TABLE 2

|  | Conversion of terephthalic acid | MHET/BHET (molar ratio) |
|---|---|---|
| Ex. 1 | 99% | 0 |
| Ex. 2 | 88.28% | 0.0145 |
| Ex. 3 | 73.5% | 0.0336 |
| Ex. 4 | 63.82% | 0.0152 |
| Ex. 5 | 88% | 0.0243 |
| Ex. 6 | 88.1% | 0 |
| Comp. Ex. 1 | 56.5% | 0.0534 |
| Comp. Ex. 2 | 46.4% | 0.0497 |

As shown in Table 2, in each of Examples 1-6, conversion of terephthalic acid is above 63% and a molar ratio of MHET/BHET is below 0.035. Specifically, in each of Examples 1, 2, 5, and 6, conversion of terephthalic acid is above 88% and a molar ratio of MHET/BHET is below 0.025. However, in each of Comparative Examples 1 and 2, conversion of terephthalic acid is below 57% and a molar ratio of MHET/BHET is above 0.045.

In addition, the amount of waste solvent (i.e., the total amount of water and toluene or cyclohexane used in each of Examples 1-6) in the process according to the disclosure was reduced by at least 35% as compared to the amount of waste solvent in the process of U.S. Pat. No. 3,052,711.

In view of the aforesaid, conversion of terephthalic acid may be enhanced while the amount of MHET as a byproduct and the amount of waste solvent may be reduced by the process for preparing bis(2-hydroxyethyl) terephthalate according to the disclosure.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A process for preparing bis(2-hydroxyethyl) terephthalate, comprising a step of:
   subjecting ethylene oxide and terephthalic acid in a molar ratio of from 2:1 to 3:1 to a reaction at an elevated temperature in a range from 100° C. to 150° C. in the presence of a solvent mixture containing water and a $C_6$-$C_8$ hydrocarbon in a weight ratio of from 1:1 to 3:1.

2. The process according to claim 1, wherein the molar ratio is from 2.7:1 to 3:1.

3. The process according to claim 1, wherein the solvent mixture is in an amount from 3 to 10 mole based on 1 mole of terephthalic acid.

4. The process according to claim 1, wherein the $C_6$-$C_8$ hydrocarbon is selected from the group consisting of hexane, heptane, octane, cyclohexane, benzene, toluene, xylene, and combinations thereof.

5. The process according to claim 4, wherein the $C_6$-$C_8$ hydrocarbon is selected from the group consisting of cyclohexane, toluene, and a combination thereof.

6. The process according to claim 1, wherein the reaction is performed in the presence of a base.

7. The process according to claim 6, wherein the base is selected from the group consisting of sodium carbonate, potassium carbonate, sodium hydroxide, potassium hydroxide, amine, an organic ammonium salt, an inorganic ammonium salt, and combinations thereof.

8. The process according to claim 1, wherein the subjecting step is implemented by combining terephthalic acid with the solvent mixture to form a combination and adding ethylene oxide to the combination slowly at the elevated temperature.

9. The process according to claim 1, further comprising a step of removing the solvent mixture after the reaction.

* * * * *